United States Patent [19]
Band et al.

[11] Patent Number: 5,153,174
[45] Date of Patent: Oct. 6, 1992

[54] POLYMER MIXTURES USEFUL IN SKIN CARE

[75] Inventors: Philip A. Band, Brooklyn, N.Y.;
Arminda G. Barbone, Union, N.J.;
Errol D. Goddard, Haworth, N.J.;
Adolf Leshchiner, Cresskill, N.J.;
Emmett M. Partain, III, Bound Brook, N.J.; Joseph P. Pavlichko, Helmetta, N.J.

[73] Assignees: Union Carbide Chemicals & Plastics Inc., Danbury, Conn.; Biomatrix Incorporated, Ridgefield, N.J.

[21] Appl. No.: 428,782

[22] Filed: Oct. 30, 1989

[51] Int. Cl.$^5$ .......................... A61K 7/00; A61K 37/02
[52] U.S. Cl. ................................... 514/12; 424/78.02; 424/78.03; 424/401; 424/488; 514/2; 514/21; 514/44; 514/59; 514/776; 514/844; 530/362; 530/363
[58] Field of Search ................. 514/54, 773, 781, 776, 514/2, 12, 21, 44, 844, 59; 424/28, 484, 485, 488, 401, 78.03; 530/362, 363

[56] References Cited

U.S. PATENT DOCUMENTS

| | | |
|---|---|---|
| 3,523,998 | 8/1970 | Feinstone ........................ 424/78 |
| 4,303,670 | 12/1981 | Balazs . |
| 4,486,416 | 12/1984 | Soll et al. ........................ 514/54 |
| 4,582,865 | 4/1986 | Balazs et al. .................... 514/781 |
| 4,605,691 | 8/1986 | Balazs et al. .................... 524/27 |
| 4,636,524 | 1/1987 | Balazs et al. .................... 514/281 |
| 4,767,463 | 8/1988 | Brode et al. . |
| 4,965,071 | 10/1990 | Kawan ........................... 424/78 |

FOREIGN PATENT DOCUMENTS 62-51604 3/1987 Japan .
62-51605 3/1987 Japan .

OTHER PUBLICATIONS

Shiseido Ku, WPI Abstract, JP 62 051605 Mar. 6, 1987.
Kligman, "Albumin as Antiwrinkling Cosmetic", J. Soc. Cosmetic Chemist, 16, 557–562 (1965).
P. Band, "Effective Use of Hyaluronic Acid", *Drug and Cosmetic Industry*, vol. 137, p. 54 (Oct. 1985).
M. Rieger, "The Apparent pH on the Skin", *Cosmetics & Toiletries*, vol. 104, pp. 53–60 (Mar. 1989).
A. G. Ogston, "Some Thermodynamic Relationships in Ternary Systems, with Special Reference to the Properties of Systems Containing Hyaluronic Acid and Protein", *Archives of Biochemistry and Biophysics*, Supplement 1, 39–51 (1962).

Primary Examiner—Merrell C. Cashion, Jr.
Assistant Examiner—Andrew G. Rozycki
Attorney, Agent, or Firm—W. K. Volles

[57] ABSTRACT

Binary polymer mixtures of albumin and glycosaminoglycan and ternary polymer mixtures of polyionic polypeptide and high molecular weight and highly charged polyanions are useful for managing skin including wrinkles or other irregularities. Aqueous compositions of the ternary mixtures have pH dependent phase change properties and provide skin activated films.

14 Claims, 3 Drawing Sheets

FIG. 7
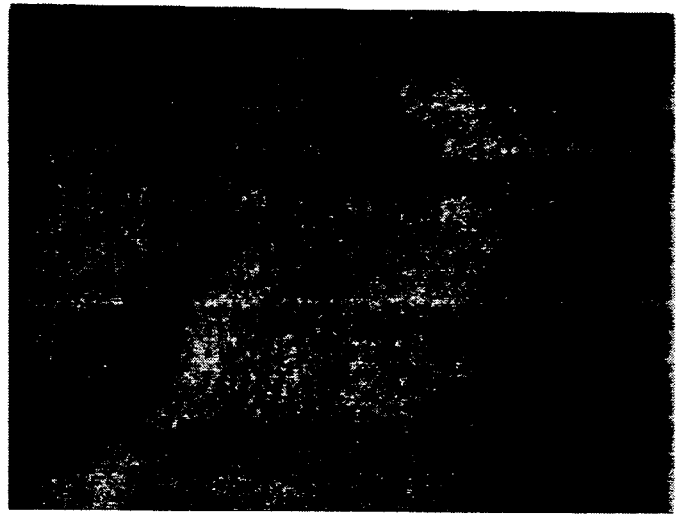
FIG. 8

POLYMER MIXTURES USEFUL IN SKIN CARE

BACKGROUND OF THE INVENTION

1. Field of the Invention

This invention relates to polymeric compositions and their use for managing skin and more particularly to specific binary and ternary polymer compositions and processes in skin care.

2. Description of Background Information

Skin is frequently in a condition for which treatment or some other managing remedy is needed or desired. For example, a common skin concern involves wrinkles or other irregularities. Many substances have been applied to skin in order to alleviate skin conditions. Among the myriad of such substances, a wide variety of polymers have been used, such as polyanions, i.e. anionic or negatively charged polymers. For example, skin care using hyaluronan, a polyanion and glycosaminoglycan, is described in U.S. Pat. No. 4,303,676 (Balazs) and an article by P. Band entitled "Effective Use of Hyaluronic Acid", in *Drug and Cosmetic Industry*, Volume 137, page 54, October 1985. Dextran sulfate, a highly charged polyanion, is disclosed in skin care applications in Japanese Laid-open (Kokai) Patent Applications No. 62-051,604 and No. 62-051,605. Various polyionic polypeptides have also been used in skin care. For example, skin care using bovine serum albumin, a polyionic polypeptide, is described by A. M. Kligman and C. M. Papa in an article entitled "Albumin as an Antiwrinkling Cosmetic", in the *Journal of the Society of Cosmetic Chemists*, Volume 16, pages 557-562 (1965). While this study discusses the utility provided by albumin as an antiwrinkling cosmetic, such activity is limited by: elimination through working, i.e. lacking in substantivity; nullification by skin movement; lack of cumulative action; limited permeability; limited utility at low use levels; and film visibility and poor film properties, such as scaling or flaking, at higher use levels.

The ability of substances used to treat skin can be influenced by the properties of the skin. For instance, skin is normally acidic, characterized by a pH of around 5 to 6. A discussion of skin acidity and the influence of substances applied to the skin is discussed in an article by M. Rieger entitled "The Apparent pH on the Skin" in *Cosmetics & Toiletries*, Volume 104, pages 53-60, March 1989.

It would be desirable if there were compositions and processes which provide improved treatment or management of skin and which take advantage of its properties upon application. For example, significant benefits would be provided by improved compositions and processes for managing skin irregularities, such as diminishing the appearance of wrinkles, and/or which are activated by the skin upon application.

SUMMARY OF THE INVENTION

This invention pertains to binary and ternary polymer mixtures, and aqueous compositions thereof containing water. The ternary polymer mixtures comprise mutually distinct components selected from each of the following groups:

(1) polyionic polypeptide;
(2) first, high molecular weight, polyanion having a molecular weight of at least about 100,000; and
(3) second, highly charged, polyanion containing acidic groups with a $pK_1$ of less than about 3 in an amount sufficient to provide an equivalent weight of such acidic groups of less than about 1,000;

which mixture provides pH dependent phase change in aqueous solution due to interactions between the three components. Personal care compositions and processes for managing skin, including processes for diminishing the appearance of wrinkles or other irregular areas of the skin, by applying an effective managing amount of such ternary polymer mixtures to skin, with carrier and with or without suitable skin care additives, are also provided. Skin care compositions and processes using binary polymer mixtures of albumin and glycosaminoglycans are also provided.

BRIEF DESCRIPTION OF THE DRAWINGS

FIGS. 1 through 8 are photographs of skin and other substrates treated with compositions of polymer mixtures of this invention or comparative controls, as hereinafter discussed.

DETAILED DESCRIPTION OF THE INVENTION

Figure 1:
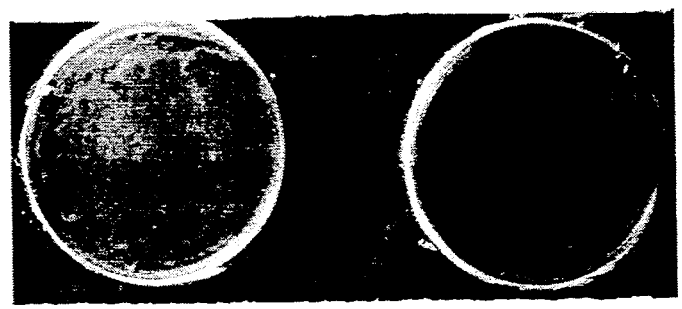

The ternary polymer mixture is made up of mutually distinct components, i.e. polypeptide and polyanions where each differs from the other two components. Since the three groups or classes of polymers overlap, i.e. some polymers are members of more than one group, when one or more components is used which is a member of more than one of the three groups of polymers, such as a polynucleotide which is both a high molecular weight and highly charged polyanion, such component(s) is or are selected as being from the group(s) necessary to provide a mixture having components from each of three classes of polymers. For example, DNA as used in the examples is both a high molecular weight and highly charged polyanion, i.e. a member of both the second or third class of polymers in the ternary polymer mixtures of this invention. In Example 49, DNA is provided as the high molecular polyanion while dextran sulfate is used as the highly charged polyanion. In Example 91, DNA is provided as the highly charged polyanion while hyaluronan is used as the high molecular weight polyanion. For ternary polymer mixtures having two or more components which are members of more than one of the three classes of polymers, such as mixtures of polyionic polypeptide and two kinds of polynucleotides each of which are both high molecular weight and highly charged polyanions, the multiclass components represent different classes of components such that at least one from each of the three classes of polymers is provided. In such mixtures, the multiclass components must differ from each other, i.e. are mutually distinct, and are generally sufficiently different to provide ternary polymer mixtures characterized by the designated pH dependent phase change or skin care utilities.

For the ternary polymer mixtures of this invention, the kinds of polyionic polypeptide and polyanions provided are not narrowly critical. In the broadest sense, any polyionic polypeptide, any high molecular weight polyanion and any highly charged polyanion may be used which when combined provide the designated pH dependent phase change properties and/or utility for managing skin. For the binary polymer mixtures, albumin, a polyionic polypeptide and glycosaminoglycan, a polyanion, are provided.

Polyionic polypeptides may be selected from any polyionic polypeptides, such as those useful in skin applications, including, but not limited to, materials described in an article by G. Schuster and L. A. Domsch entitled "Protein Chemistry as Related to Cosmetics and Toiletries" in *Cosmetics and Toiletries*, Volume 99, pages 63-74, December 1984; and an article by R. R. Riso entitled "Protein derivatives in cosmetics" in *Cosmetics and Perfumery*, Volume 89, pages 45-48, April 1974. The term "polypeptide" as used herein pertains to compounds containing repeating peptide linkages, such as proteins and their derivatives. Polyionic polypeptides are polypeptides which have multiple ionized groups. The polypeptide may contain conjugated materials such as carbohydrates, as in glycoproteins, or lipids, as in lipoproteins. The polypeptide is not limited to any secondary, tertiary or quaternary structure, and may, for example, be extended, folded, helical, coiled or globular. The polyionic polypeptide is generally a highly charged protein, having an isoelectric point of between about 3 to about 10 and preferably comparable to the pH characteristic of skin of around 4 to 6. The polypeptide is generally soluble in salt-free, aqueous solution and may exhibit utility for smoothing or filling skin irregularities.

In the broadest sense, albumin, as provided in the binary polymer mixture, comprises any protein soluble in 50% saturated ammonium sulfate and which generally remains soluble in such solution even in the absence of salts, such as removed by dialysis. A more detailed description of albumins is given by F. Haurowitz, in *Chemistry and Biology of Proteins*, First Edition, Academic Press Inc., New York, 1950, in Chapter VIII beginning on page 148.

Illustrative polyionic polypeptide which may be provided include, but are not limited to, one or more of the following: albumin, such as from egg or animal, e.g. bovine, serum; derivatized collagen polypeptides, such as Cationic Collagen Polypeptides available from Amerchol Corporation; elastin; globulin polypeptide, such as myoglobin; and derivatives of such proteinaceous or other materials, such as keratin. A particularly preferred polyionic polypeptide is serum albumin.

Polyanions may be selected from any high molecular weight and highly charged polyanions, such as those useful in skin applications. The weight average molecular weight of the high molecular weight polyanion is greater than about 100,000, preferably from about 500,000 to about 20,000,000, and most preferably from about 1,000,000 to about 10,000,000. The highly charged polyanion contains a plurality of acidic groups which: (1) have a dissociation constant, i.e. $pK_a$, of less than about 3, preferably less than about 2, and most preferably less than about 1.5; and (2) are present in an amount sufficient to provide an anionic charge density in terms of an equivalent weight, defined as the weight average molecular weight of the polyanion per such acidic group of salt thereof, of less than about 1,000, preferably from about 100 to about 500, and most preferably from about 100 to about 350. The highly charged polyanion also generally has a molecular weight sufficient to provide the requisite utility or pH dependent phase change interaction when combined with the polyionic polypeptide and high molecular weight polyanion. Accordingly, the highly charged polyanion generally has a weight average molecular weight of at least about 40,000, preferably from about 50,000 to about 5,000,000, and most preferably 100,000 to about 1,000,000.

Representative high molecular weight polyanions which may be provided include, but are not limited to, one or more of the following: polynucleotides such as deoxyribonucleic acid, i.e. DNA, and ribonucleic acid, i.e. RNA; and polycarboxylates including: hyaluronan, such as hylan, or their derivatives; xanthan gum and anionic cellulosics, such as sodium carboxymethyl cellulose. Particularly preferred high molecular weight polyanion is hyaluronan or derivatives thereof. Hyaluronan, and derivatives thereof, contain repeating disaccharide structure of D-glucuronic acid and 2-acetamido-2-desoxy-D-glucose joined by alternating $\beta$1-3 glucoronidic and $\beta$1-4 glucosaminidic bonds.

Glycosaminoglycans are well known, naturally occurring, polysaccharides containing disaccharide repeating units of hexosamine and hexose or hexuronic acid, and may contain sulfate groups. The size, type or form of glycosaminoglycan provided is not narrowly critical to this invention. The molecular weight of the glycosaminoglycan is not critical to the binary polymer mixture and may range from about 5,000 to about 20,000,000, preferably from about 100,000 to about 12,000,000, and most preferably from about 1,000,000 to about 10,000,000.

The glycosaminoglycan or hyaluronan may be provided in free acid or salt form and may be associated with any suitable cation, including, but not limited to: alkali metals, such as sodium and potassium; alkaline earth metals; nitrogen-containing cations, such as ammonium, substituted ammonium and quaternized derivatives thereof; and other suitable cations. Preferred salts of glycosaminoglycans or hyaluronans, and derivatives thereof, include alkali metal or alkaline earth metal glycosaminoglycates and hyaluronates. The glycosaminoglycan or hyaluronan may be provided: in pure form; as a mixture of glycosaminoglycan or hyaluronan with proteins and naturally occurring substances derived by the production of glycosaminoglycan or hyaluronan from natural material; or as a chemically modified, glycosaminoglycan or hyaluronan derivative. Mixtures of such glycosaminoglycans or hyaluronans may also be provided.

Representative glycosaminoglycans include, but are not limited to, one or more of the following: hyaluronan or derivatives thereof such as hylan; heparin; heparan; chondroitin; keratan; dermatan; and sulfates of such materials.

Representative hyaluronan and derivatives thereof which may be provided include, but are not limited to, one or more of the following: BIOMATRIX* hyaluronan provided by Biomatrix, Inc., such as described in U.S. Pat. No. 4,303,676 (Balazs) which is incorporated herein by reference, HYLADERM* hylan provided by Biomatrix, Inc., such as described in U.S. Pat. No. 4,713,448 (Balazs, et al.) which is incorporated herein by reference; and substantially pure hyaluronan such as described in U.S. Pat. No. 4,141,973 (Balazs) which is incorporated herein by reference.

Representative highly charged polyanions which may be provided include, but are not limited to, one or more of the following; polysulfonates; polysulfates, such as dextran sulfate and poly(vinyl) sulfate; and polynucleotides, such as DNA. Particularly preferred highly charged polyanion is dextran sulfate.

The specific and relative amounts of polypeptide, or albumin, and polyanions, or glycosaminoglycan, provided are not narrowly critical. In the broadest sense: each ternary polymer component is present in specific and relative amounts sufficient to provide pH dependent phase change properties and/or skin care utility, and each binary polymer component is present in specific and relative amounts sufficient to provide interactive skin care utility. Generally, for skin care use an effective managing amount, defined as those amounts of each and both or all three of the Polymer components sufficient to provide a composition with utility upon application to skin, is provided. In aqueous compositions, the amount of polypeptide or albumin is typically at least about 0.01 wt. %, preferably from about 0.05 wt. % to about 30 wt. %, and most preferably from about 0.1 wt. % to about 20 wt. % of the composition. The amount of high molecular weight polyanion or glycosaminoglycan is typically at least about 0.001 wt. %, preferably from about 0.01 wt. % to about 2 wt. %, and most preferably from about 0.05 wt. % to about 1 wt. % of the composition. The amount of highly charged polyanion is typically at least about 0.001 wt. %, preferably from about 0.01 wt. % to about 2 wt. %, and most preferably from about 0.05 wt. % to about 1 wt. % of the composition. The balance of the aqueous composition, i.e. up to about 99 wt. %, is water plus any optional materials. For ternary polymer mixtures: the relative weight ratio of polypeptide to high molecular weight polyanion will typically range from about 0.05:1 to about 100:1, preferably from about 0.1:1 to about 100:1, and most preferably from about 0.5:1 to about 70:1; the relative weight ratio of polypeptide to highly charged polyanion will typically change from about 1:1 to about 200:1, preferably from about 2:1 to about 100:1 and most preferably from about 3:1 to about 50:1; and the relative weight ratio of highly charged polyanion to high molecular weight polyanion will typically range from about 0.1:1 to about 100:1, preferably from about 0.2:1 to about 50:1 and most preferably from about 0.5:1 to about 10:1. For binary polymer mixtures, the relative weight ratio of albumin to glycosaminoglycan will typically range from 0.05:1 to about 200:1, preferably from about 0.1:1 to about 100:1, and most preferably from about 0.5:1 to about 70:1.

The ternary polymer mixture provides pH dependent phase change properties due to interactions between the three components, as opposed to simply the properties or interactions of any one or two of the components. Accordingly, pH dependent phase change values for the ternary polymer mixture differing from corresponding values for only one or two of the components indicate pH dependency derived from ternary component interactions. These properties are generally exhibited by measuring the amount of light transmitted through aqueous solutions of such ternary polymer mixtures at different pH conditions. This pH dependent, light transmission characteristic is generally exhibited by aqueous solutions of the ternary polymer mixture in water alone or along with other components. Any other components present, however, which interfere with the light transmission measurements, either directly by interfering with light transmission or indirectly by interacting with the mixture, should be neutralized or otherwise isolated for unimpaired light transmission measurement. The pH dependent light transmission can be demonstrated by comparing the transmission of visible light through aqueous solutions of the ternary polymer mixture determined under acidic, such as a pH of around 5 to 6 for normal skin, versus neutral, i.e. pH of 7, conditions. The amount of decreased transmission provided is not narrowly critical. In general, the amount of light transmitted under acidic conditions may be from just slightly below up to many times less than the transmission of light through the composition under neutral conditions. The particular manner for determining transmission is not narrowly critical. For example, transmission can be measured at a wavelength of light of 540 nanometers using a Pye Unicam 8610 UV visible spectrophotometer, in a one centimeter pathlength cell.

The ternary polymer mixture may exhibit other desirable or exceptional properties. In one embodiment, aqueous solutions of the ternary polymer mixture exhibit liquid-phase separation. Such phenomenon is discussed in Chapter 2 entitled "Aqueous Polymer-Phase Systems", on pages 8-39, of a text by P. A. Albertsson entitled *Partition of Cell Particles and Macromolecules*, published by John Wiley & Sons, New York, 1976. Since aqueous solutions of the ternary polymer mixtures contain polyionic polypeptides and two types of anionic polymers, polyphase (generally biphase) formation occurs as a result of polymer incompatibility and coacervation properties and is influenced by interactions between the various ionic groups, molecular weight and other characteristics of the polymers. In some embodiments, the concentration of polymers between phases is pH dependent and gives another measure of pH dependent phase change properties. In such instances, a difference in concentrations of one or more of the polymers between the liquid phases as determined under acidic, such as a pH of around 5 to 6 for normal skin, versus neutral, i.e. pH of 7, conditions, provides a means for characterizing the ternary polymer mixtures. In some instances, pH dependent phase changes may also be exhibited by: differences in turbidity; the formation or elimination of liquid-phase separations; or other physical or chemical modifications occurring with a change in pH.

The pH sensitivity of the ternary polymer mixtures can be advantageously used in skin care. For example, skin care compositions containing the ternary polymer mixture may be formulated to have a pH other than the pH of skin, e.g by having neutral pH of around 7. Upon application to skin and its accompanying acidic conditions, the pH sensitive properties of the composition can be designed to assist the utility of the composition. Such compositions would therefore be "skin activated". Illustrative skin utility may include: assisting in formation of films with cosmetically desirable, optical properties upon skin application, such as decreasing flaking and drying of the film; enhancing deposition of the ternary components or other additives provided to the skin; improving desirable skin feel and characteristics, such as moisturization and smoothening; optimizing aesthetic and cosmetic attributes of the binary or ternary polymer components, such as dry down; and effacement of wrinkles by physical action of films containing the polymer mixture applied to the skin surface.

For example, for ternary polymer mixtures which exhibit turbidity as a pH dependent phase change, clear gels of such mixtures can be used to provide translucent films upon application to the skin. It has been found that the pH dependent increase in turbidity is indicative of the pH dependent film-forming properties of these compositions.

Skin care utility provided by the binary or ternary polymer mixture may include enhanced performance properties for compositions containing such mixture when applied to the skin. Enhanced spreadability, as well as increased smoothing and uniformity, can be provided in, for example, make-up formulations. In addition, such polymer complexes demonstrate a rheological synergy contributing to the smoothening effects manifested as improved rub-in and afterfeel. Enhanced keratin substantivity of hyaluronan, as high molecular weight polyanion, is also achieved providing long lasting hydration and/or moisturization of the skin due to the highly hygroscopic properties of hyaluronan. The polymer mixtures can optimize the benefits of each single component within the mixture in a complementary and synergistic way while visibly improving the inherent esthetic properties of such components, including maintaining a natural skin feel and appearance. Improved solubility can be provided for polyionic polypeptides when provided in the ternary polymer mixture, as opposed to being provided alone, such as by decreasing polypeptide sedimentation in, for example, gel or toner formulations.

The binary and ternary polymer mixtures, and their aqueous compositions, may provide utility not only in skin care, but in other areas of cosmetics, in health care, in biological separations, in colorless paper or in any application benefiting from the pH dependent properties for the polymer mixture.

The binary or ternary polymer mixture may be provided in a suitable carrier, or mixtures of carriers, which acts as a fluid vehicle for the composition, and either alone or in combination with suitable, optional ingredients. The type of carrier is not critical and may be selected from any carrier suitable to the particular application. Illustrative carriers include, but are not limited to: water, such as deionized or distilled water; emulsions, such as oil-in-water or water-in-oil emulsions; alcohols, such as ethanol, isopropanol or the like; glycols, such as propylene glycol, glycerine or the like; and combinations thereof. Preferred carrier systems include water-in-oil or oil-in-water emulsions, water, ethanol and aqueous ethanol mixtures.

Optional ingredients or additives which may be added to the binary or ternary polymer mixtures can be selected from any suitable substance which may be used to manage skin. Highly charged polyanions, as well as polyionic polypeptides other than albumin and high molecular weight polyanions other than glycosaminoglycans, would be optional components of the binary polymer mixture. While it is expected that the binary and ternary polymer mixtures would exhibit the pH dependent properties and/or skin care utility in the presence of a number of different types of optional ingredients, it is anticipated that non-ionized and relatively non-polar additives, including water-insoluble materials, are least likely to adversely affect the properties of the polymer mixtures. However, in practice the influence of any optional ingredients upon the utility of the polymer mixtures would have to be assessed, particularly in adding ionic surfactants or other ingredients which associate or interfere with similarly or oppositely charged polymers of the binary or ternary mixtures. Accordingly, special care should be taken when formulating so as not to affect the binary or ternary polymer complexes to render them ineffective. Except for any incompatible ingredients, i.e. additives which when combined with the binary or ternary mixtures produce the previously noted interference in polymer utility, illustrative optional ingredients may include, but are not limited to, one or more of the following.

Illustrative surfactants may include: anionics including fatty acid soaps, alkyl sulfates, alkyl ether sulfates, alkyl aryl sulfonates, sarcosinates, alkyl glucose esters or their alkoxylates and in particular sodium lauryl sulfate, ammonium lauryl sulfate, triethanolamine lauryl sulfate, sodium laureth sulfate, triethanolamine stearate; nonionics including methyl glucose stearates or their ethoxylates and glycerol monostearate, fatty acid alkanol amides, alkyl aryl polyglycol ether, polyglycol ethers and in particular cocoyl diethanolamide, nonoxynol-7 and octoxynol-9; cationics including alkyl trimethyl ammonium salts, quaternized amides of ethylene diamine, alkyl pyridinium salts and in particular cetrimonium chloride, stearalkonium chloride and cetyl pyridinium chloride; and amphoterics including alkyl $\beta$-aminopropionates, betaines, alkyl imidazolines and in partiCular cocamidopropyl betaine and caproamphocarboxy proPionate. Illustrative cleansing oils or the like may include natural oils and alcohols and in particular mineral oil, lanolin oil, jojoba oil, sesame oil, ethanol and isopropanol. Illustrative colorants may include pigments, dyes, and in particular FD&C Blue No. 1, FD&C No. 1 Aluminum Lake or similar sets of green, red or yellow. Illustrative preservatives may include alcohols, aldehydes, p-hydroxybenzoates and in particular methylparaben, propylparaben, glutaraldehyde and ethyl alcohol. Illustrative moisturizers may include 2-pyrrolidone-5-carboxylic acid and its salts and esters, alkyl glucose alkoxylates or their esters, fatty alcohols, fatty esters, glycols and in particular methyl glucose ethoxylates or propoxylates and their stearate esters, isopropyl myristate, lanolin or cetyl alcohols, aloe, silicones, propylene glycol, glycerol and sorbitol. Illustrative pH adjustors may include inorganic and organic acids and bases and in particular aqueous ammonia, citric acid, phosphoric acid, acetic acid, triethanolamine and sodium hydroxide. Illustrative emulsifiers may include anionic and nonionic surfactants and in particular stearic acid, glycerol monostearate, cocoyl diethanolamide, and the particular anionic and nonionic surfactants listed previously. Illustrative propellants may include hydrocarbons, fluorocarbons, ethers, carbon dioxide, nitrogen and dimethyl ether. Illustrative reducing agents may include ammonium thioglycolate and sodium thioglycolate. Illustrative thickeners may include salts and cellulosics and in particular sodium chloride, water soluble cellulose derivatives such as hydroxyethyl cellulose, and associative thickening polymers.

Other typical ingredients may include, but may not be limited to, one or more of the following: fragrances; foaming agents; sunscreen and suntan agents; depilatory agents; flavors; astringent agents; antiseptics; deodorants; antiperspirants; insect repellants; bleaches and lighteners; anti-dandruff agents; adhesives; polishes; strengtheners; fillers; barrier materials; and other skin care additives.

The amount of optional ingredients contained in the composition is not critical but will vary depending upon the particular ingredient, composition and desired use level and may be any effective amount for achieving the desired property provided by such ingredients, following established procedures.

The binary or ternary polymer mixture may be Produced by providing the polypeptide, or albumin and polyanions, or glycosaminoglycan, along with one or more optional ingredients as previously described, in one or more suitable carriers, using standard procedures.

In a typical embodiment, aqueous solutions of either albumin and glycosaminoglycan for binary polymer mixtures or polyionic polypeptides, high molecular weight and highly charged polyanions for ternary polymer mixtures are obtained and added together to form the binary or ternary polymer mixture, respectively. These mixtures may then be combined with suitable skin care additives or other optional ingredients to provide skin care formulations or other useful compositions, such as for skin care including diminishing the appearance of wrinkles or other irregular areas of the skin, using established techniques.

The following examples are presented as illustrative embodiments of this invention and are not intended to limit the scope thereof. Control examples are generally identified by a "C" suffix. All of the parts, percentages and proportions referred to herein, including the claims, are by weight unless otherwise indicated.

EXAMPLES

The various designations used in the examples are defined as follows:

| Designation | Description |
|---|---|
| BSA | Bovine serum albumin, a polyionic polypeptide, which unless otherwise indicated dissolves in water to give a pH of about 7 and is available from Waitaki International Biosciences as product #16349. |
| CCP | Hydrolyzed collagen polypeptides, polyionic polypeptides, with an isoionic point above 8, available from Amerchol Corporation under the trademark CATIONIC COLLAGEN POLYPEPTIDES ®. |
| ChS | Chondroitin sulfate, a sulfated glycosaminoglycan, which unless otherwise indicated is available from Sigma Chemical Co. as product #C-4134. |
| $CMC_H$ | Sodium carboxymethylcellulose, a high molecular weight polyanion, prepared from cotton linters by the procedure described in Macromolecular Synthesis, Collective Volume 1, edited by J. A. Moore, J. Wiley, 1977, having a degree of substitution of carboxy substituents of 0.9 and a molecular weight of 1-2 million. |
| $CMC_M$ | Sodium carboxymethylcellulose, a high molecular weight polyanion, having a degree of substitution of carboxy substituents of 0.9 and a molecular weight of 0.6-0.7 million available from Hercules Inc. under the trademark CELLULOSE GUM ®. |
| Dex | Dextran, having a molecular weight of between 2 to 12 million, available from Pharmachem as Dextran - purified crude grade 3P. |
| DNA | Deoxyribonucleic acid, a polynucleotide and both high molecular weight and highly charged polyanion, Type III obtained from salmon testes having an equivilent weight per sodium phosphate groups of about 332, available from Sigma Chemical Co. as product #D-1626. |
| DxS | Dextran sulfate, a highly charged polyanion, which unless otherwise indicated has an equivalent weight of sodium sulfate groups of about 180 and a molecular weight of about 500,000, and is available from Pharmacia AB as Dextran sulfate sodium salt, catalogue #17-0340-01. |
| $DxS_L$ | A low molecular weight dextran sulfate, a highly charged polyanion, having an equivalent weight per sodium sulfate groups of about 180 and a molecular weight of about 5,000 available from Sigma Chemical Co., as product #D-0768. |
| EDTA | Ethylenediaminetetraacetate, available from Dow Chemical Co. under the trademark VERSENE ®. |
| Egalb | Egg albumin, a polyionic polypeptide, in either crude or purified form as specified, available from Sigma Chemical Co. under product #A-5253 and #A-5503, respectively. |
| GERMABEN | A broad spectrum preservative containing diazolidinyl urea, methyl paraben and propyl paraben in a propylene glycol base, available from Sutton Laboratories under the trademark GERMABEN ® II. |
| GLUCAM E10 | 10 mole ethoxylate of methyl glucose, available from Amerchol Corporation under the trademark GLUCAM ® E10. |
| GLUCAM E20 | 20 mole ethoxylate of methyl glucose, available from Amerchol Corporation under the trademark GLUCAM ® E-20. |
| GLUCAM E20DS | 20 mole ethoxylated of methyl glucose distearate ether, available from Amerchol Corporation under the trademark GLUCAM ® E-20 DISTEARATE. |
| GLUCAM P10 | 10 mole propoxylate of methylglucose, available from Amerchol Corporation under the trademark GLUCAM ® P-10. |
| GLUCAM P20 | 20 mole propoxylate of methyl glucose, available from Amerchol Corporation under the trademark GLUCAM* P-20. |
| GLUCAM P20DS | 20 mole propoxylate of methyl glucose distearate ether, available from Amerchol Corporation under the trademark GLUCAM ® P-20 DISTEARATE. |
| HA | A relatively low molecular weight hyaluronan, a glycosaminoglycan, having a molecular weight of less than 500,000, available from Sigma Chemical Co. as product #H-1751. |
| $HA_{bact}$ | A relatively low molecular weight hyaluronan, a glycosaminoglycan, made by bacteria and having a molecular weight of less than 500,000, available from Lifecore Biomedical as hyaluronic acid for in vitro use only. |
| HD | Sodium salt of hylan, a glycosaminoglycan and high molecular weight polyanion, produced by in-situ reaction of aldehyde with naturally occurring hyaluronan in rooster comb, following the procedures described in U.S. Pat. No. 4,713,448, having a intrinsic viscosity number in excess of 4,000 cc per gram (measured at 80 mg per ml. of glycosaminoglycan in a 0.15N sodium chloride solvent at 20° C., available from Biomatrix, Inc. under the trademark HYLADERM ®. |
| HEALON | An ultrpure hyaluronan fraction, a glycosaminoglycan, having a molecular weight of 3-4 million, available from Pharmacia AB under the trademark HEALON ®. |
| Hep | Heparin, a highly charged polyanion and sulfated glycosaminoglycan, having an equivalent weight of sodium sulfate groups of about 188 and a molecular weight of 10-20 thousand, available from Sigma Chemical Co. as product #3125. |
| Lys | Lysosyme, a polyionic polypeptide, having an isoelectric point greater than pH 10, available from Sigma Chemical Co. as product #L-6876. |
| Mglob | Myoglobin, a polyionic polypeptide, obtained from horse skeletal muscle, available from Sigma Chemical Co. as product #M-0630. |
| PABA | Para amino benzoic acid, a sunscreen, available from Nipa Laboratories under the trademark NIPA ® PABA. |
| Pacr | Polyacrylic acid, having a molecular |

-continued

| Designation | Description |
|---|---|
| | weight of about 4 million, available from B. F. Goodrich under the trademark CARBOPOL ® 940. |
| PEG$_H$ | Polyoxyethylene, having a molecular weight of about 5 million available from Union Carbide Chemicals and Plastics Company Inc. under the trademark POLYOX ® WSR COAGULANT. |
| PEG$_L$ | Polyoxyethylene, having a molecular weight of about 400 available from Sigma Chemical Co. as product #P-3265. |
| PEG$_{N10}$, PEG$_{N30}$ and PEG$_{N60}$ | Polyoxyethylenes, having molecular weights of about 100,000, 400,000 and 600,000 respectively, available from Union Carbide Chemicals and Plastics Company Inc. under the trademarks POLYOX ® WSR N-10, POLYOX ® WSR N-3000 and POLYOX ® WSR N-60-K, respectively. |
| P—L—Arg | Poly-L-arginine, HCl salt, a polyionic polypeptide, having a molecular weight of about 100,000, available from Sigma Chemical Co. as product #P-3892. |
| PVA | Polyvinyl alcohol, having a molecular weight of about 40,000, available from Sigma Chemical Co. as product #P-1763. |
| PVP | Polyvinyl pyrrolidone, having a molecular weight of about 360,000, available from Aldrich Chemical Co. under product #85, 656-8. |
| PVS | Polyvinyl sulfate, a highly charged polyanion, having an equivalent weight per sodium sulfate groups of about 162 and a molecular weight of about 350,000 available from Kodak Co. under catalogue #1199678. |
| TEA | Triethanolamine. |
| Xan | Xanthan gum, a high molecular weight polyanion, an exocellular polysaccharide, having a molecular weight of greater than 2 million, available from Kelco Inc. under the trademark KELTROL ®. |

Unless otherwise indicated, the following test procedures are used to measure product and performance characteristics listed in the examples.

Light Transmission: After cleared of air bubbles, samples of aqueous solutions of the specified material are measured for visible absorbance, at a wavelength of 540 nanometers, using a spectrophotometer and distilled water as a control.

Radiolabelled Measurement: The specified composition is transferred to a 20 ml glass Scintillation vial with and then 10 ml of Scintillation Cocktail is added. The radioactivity of the material is detected using an ISO-CAP ® 300 liquid scintillation counter. The amount of radioactive material is measured in counts per minute from which disintegrations per minute, i.e. DPM is calculated.

EXAMPLES 1-114

Light Transmission Evaluation

Aqueous solutions of various polymers are evaluated using the previously described light transmission test, with the results set forth in Tables 1 and 2.

Examples 1-13 demonstrate the pH dependent phase change properties of various ternary polymer mixtures, shown by increased light absorbance values under acidic, i.e., less than pH of 7 versus neutral, i.e., pH of 7, conditions.

Examples 14-27 demonstrate pH dependent phase change properties for ternary polymer mixtures of varying polymer concentrations.

Examples 28-40 demonstrate pH dependent phase change properties for ternary polymer mixtures for a variety of preferred polymer species.

Examples 41-58 demonstrate pH dependent phase change properties for polymer mixtures containing a variety of high molecular weight polyanions or substitute materials.

Examples 59-70 demonstrate pH dependent phase change properties for polymer mixtures containing a variety of polyionic polypeptides or substitute materials.

Examples 71-104 demonstrate dependent phase change properties for polymer mixtures containing a variety of highly charged polyanions or substitute materials.

Example 105 demonstrates pH dependent phase properties for ternary polymer mixtures containing preservative.

Examples 106-114 demonstrate pH dependent phase change properties for pH adjusted polymer compositions.

EXAMPLES 115-137

Phase Distribution Evaluation

The concentration of polymer components in the top and bottom phases of biphase solutions is set forth in Table 3. In Examples 134 to 137, initial hyaluronan concentrations prior to centrifugation of 0.40, 0.41, 0.34 and 0.44 mg/ml, respectively, are used. The results demonstrate that the polyionic polypeptides, i.e. BSA, and highly charged polyanion, i.e. DxS, generally concentrate in the bottom phase whereas the high molecular weight polyanion, i.e. HD, generally concentrates in the top phase.

TABLE I

| | LIGHT TRANSMISSION DATA (pH 4.0-7.0) | | | | | | |
|---|---|---|---|---|---|---|---|
| Ex. | | Absorbance (at pH:) | | | | | |
| No. | Polymers | 4 | 4.8 | 5 | 5.2 | 5.6 | 6 | 7 |
| 1C | 0.1% HD/5% BSA | 0.064 | — | 0.054 | — | 0.071 | 0.072 | 0.070 |
| 2C | 5% BSA/1% DxA | 1.982 | 0.057 | 0.057 | 0.080 | 0.076 | 0.068 | 0.084 |
| 3 | 0.1% HD/5% BSA/1% DxS | 1.274 | 0.511 | 0.667 | 0.529 | 0.624 | 0.178 | 0.072 |
| 14C | 0.1% HD/5% BSA | 0.139 | — | 0.117 | 0.135 | — | — | — |
| 15 | 0.1% HD/5% BSA/0.01% DxS | 0.041 | — | 0.054 | 0.054 | — | — | — |
| 16 | 0.1% HD/5% BSA/0.1% DxS | 0.104 | — | 0.074 | 0.155 | — | — | — |
| 17 | 0.1% HD/5% BSA/1% DxS | 0.393 | — | 0.271 | 0.388 | — | — | — |
| 18 | 0.1% HD/5% BSA/0.1% DxS | 0.972 | 0.425 | 0.566 | 0.395 | 0.214 | 0.081 | 0.020 |
| 19 | 0.1% HD/5% BSA/0.01% DxS | 0.114 | 0.202 | 0.117 | 0.104 | 0.095 | 0.091 | 0.063 |
| 28 | 0.1% HD/5% BSA/1% DxS | 1.26 | 0.867 | 0.158 | 0.160 | 0.273 | 0.156 | 0.081 |
| 29C | 0.1% HD/5% BSA/1% DxS$_L$ | 0.332 | 0.058 | 0.026 | 0.039 | 0.026 | 0.030 | 0.032 |
| 71C | 0.1% HD/5% BSA/0.01% ChS | 0.033 | 0.103 | 0.110 | 0.074 | 0.084 | 0.157 | 0.074 |
| 72C | 0.1% HD/5% BSA/0.1% ChS | 0.104 | 0.031 | 0.043 | 0.077 | 0.120 | 0.045 | 0.055 |
| 73C | 0.1% HD/5% BSA/1% ChS | 0.951 | 0.084 | 0.087 | 0.046 | 0.058 | 0.076 | 0.046 |
| 74 | 0.1% HD/5% BSA/1% DxS | 1.26 | 0.867 | 0.158 | 0.160 | 0.273 | 0.156 | 0.081 |

TABLE 1-continued

LIGHT TRANSMISSION DATA (pH 4.0-7.0)

| Ex. No. | Polymers | Absorbance (at pH:) | | | | | | |
|---|---|---|---|---|---|---|---|---|
| | | 4 | 4.8 | 5 | 5.2 | 5.6 | 6 | 7 |
| 75C | 0.1% HD/5% BSA/1% Hep | 0.069 | 0.077 | 0.062 | 0.059 | 0.087 | 0.050 | 0.077 |
| 105 | 0.1% HD/5% BSA/1% DxS[a] | — | 1.116 | 0.959 | 0.941 | 0.625 | 0.507 | 0.089 |
| | | | | | | 0.639 (at pH 5.8) | | |

[a] With 1.5% GERMABEN and 0.2% EDTA.

TABLE 2

LIGHT TRANSMISSION DATA (pH 5.2-7.0)

| Ex. No. | Polymers | Absorbance (at pH:) | | |
|---|---|---|---|---|
| | | 5.2 | 5.6 | 7.0 |
| 4C | 5% BSA/1% DxS | 0.006 | 0.010 | 0.011 |
| 5C | 0.1% HD/5% BSA | 0.001 | 0.004 | 0.025 |
| 6C | 0.1% HD/1% DxS | 0.004 | 0.005 | 0.008 |
| 7 | 0.1% HD/5% BSA/1% DxS | 0.533 | 0.123 | 0.058 |
| 8C | 0.1% HD/5% Egalb[a] | 0.389 | 0.360 | 0.347 |
| 9C | 0.1% HD/5% CCP | 0.143 | 0.142 | 0.145 |
| 10C | 0.1% HD/2.5% CCP | 0.117 | 0.134 | 0.098 |
| 11C | 0.1% HD/1% CCP | 0.121 | 0.244 | 0.098 |
| 12C | 0.2% HD/10% BSA | 0.018 | | 0.033 |
| 13 | 0.2% HD/10% BSA/0.25% DxS | 0.503 | | 0.014 |
| 20 | 1% HD/5% BSA/0.5% DxS | 0.573 | 0.104 | 0.035 |
| 21 | 0.1% HD/5% BSA/1% DxS[b] | 0.352 | | 0.047 |
| 22 | 0.2% HD/10% BSA/2% DxS[b] | 0.440 | | — |
| 23 | 0.2% HD/10% BSA/0.5% DxS[b] | 0.778 | | 0.056 |
| 24 | 0.2% HD/10% BSA/0.25% DxS[b] | 0.531 | | 0.063 |
| 25 | 0.1% HD/5% BSA/1% DxS | 0.352 | | 0.047 |
| 26 | 0.1% HD/5% BSA/1% DxS[c] | 0.322 | | 0.026 |
| 27 | 0.1% HD/5% BSA/1% DxS[d] | 0.712 | 0.026 | |
| 30 | 0.1% HD/5% BSA[e,f]/1% DxS | — | 0.396 | — |
| 31 | 0.1% HD/5% BSA[g,h]/1% DxS | — | 0.328 | — |
| 32 | 0.1% HD/5% BSA[i,f]/1% DxS | — | 0.352 | — |
| 33 | 0.1% HD/5% BSA[j,h]/1% DxS | — | 0.218 | — |

[a] purified
[b] adjusted to pH 7.0 with NaOH
[c] Dextran Products Ltd., lot DSM-05V-46
[d] Spectrum Inc., catalogue #DE134
[e] Sigma Chemical Co. product #A3912
[f] giving pH 5.2 when dissolved in water
[g] Sigma Chemical Co. product #A7806
[h] giving pH 7.0 when dissolved in water
[i] Sigma Chemical Co. product #A8022
[j] Sigma Chemical Co. product #A9647

| Ex. No. | Polymers | 5.2 | 5.6 | 7.0 |
|---|---|---|---|---|
| 34 | 0.1% HD/5% BSA[a,b]/1% DxS | — | 0.341 | — |
| 35 | 0.1% HD/5% BSA[c,d]/1% DxS | — | 0.336 | — |
| 36 | 0.1% HD/5% BSA[e,f]/1% DxS | — | 0.376 | — |
| 37 | 0.1% HD/5% BSA[g,d]/1% DxS | — | 0.038 | — |
| 38 | 0.1% HD/5% BSA/1% DxS | — | 0.228 | — |
| 39 | 0.1% HD/5% BSA[h]/1% DxS[i] | — | 0.041 | 0.028 |
| 40 | 0.1% HD/5% BSA[j]/1% DxS[i] | 0.682 | 0.548 | 0.119 |
| 41C | 1% Dex/5% BSA/1% DxS | 0.084 | 0.097 | 0.066 |
| 42C | 1% PEG$_L$/5% BSA/1% DxS | 0.098 | 0.097 | 0.097 |
| 43 | 1% HEALON/5% BSA/1% DxS | 0.140 | 0.187 | 0.098 |
| 44C | 0.05% HA$_{bact}$/5% BSA/1% DxS | 0.129 | 0.093 | 0.080 |
| 45C | 0.1% HA$_{bact}$/5% BSA/1% DxS | 0.161 | 0.179 | 0.076 |
| 46 | 1% PVS/5% BSA/1% DxS | 0.056 | 0.032 | 0.045 |
| 47 | 1% DNA/5% BSA/1% DxS | 0.163 | 0.058 | 0.054 |
| 48 | 1% Pacr/5% BSA/1% DxS | 1.811 | 0.132 | 0.168 |
| 49C | 1% PEG$_L$/5% BSA/1% DxS | 0.043 | | 0.039 |
| 50C | 1% PEG$_{N10}$/5% BSA/1% DxS | 0.028 | | 0.030 |
| 51C | 1% PEG$_{N30}$/5% BSA/1% DxS | 0.046 | | 0.044 |
| 52C | 1% PEG$_{N60}$/5% BSA/1% DxS | 0.050 | | 0.038 |
| 53C | 1% PEG$_H$/5% BSA/1% DxS | 0.050 | | 0.024 |
| 54 | 1% HD/5% BSA/1% DxS | 0.161 | | 0.001 |
| 55 | 1% CMC$_H$/5% BSA/1% DxS | 0.161 | | 0.041 |
| 56 | 1% CMC$_M$/5% BSA/1% DxS | 0.361 | | 0.021 |

[a] Sigma Chemical Co. product #A6918
[b] giving pH 5.2 when dissolved in water
[c] Sigma Chemical Co. product #A6793
[d] giving pH 7.0 when dissolved in water
[e] Amresco Product #P0903
[f] giving pH 5.0 when dissolved in water
[g] Amresco Product #P0332
[h] Rita BOVINAL*, pH 7.0 aqueous solution
[i] containing 0.05% acetate buffer
[j] Rita BOVINAL*, pH 7.0 aqueous dialized

| Ex. No. | Polymers | 5.2 | 5.6 | 7.0 |
|---|---|---|---|---|
| 57C | 1% PEG$_H$/5% BSA/1% DxS | 0.060 | | 0.010 |
| 58 | 1% Xan/5% BSA/1% DxS | 0.278 | | 0.015 |
| 59 | 0.1% HD/5% Egalb[a]/1% DxS | 1.220[b] | 1.198[b] | 0.360[b] |
| 60 | 0.1% HD/3% Egalb[a]/1% DxS | 0.486[b] | 0.506[b] | 0.479[b] |

TABLE 2-continued
LIGHT TRANSMISSION DATA (pH 5.2-7.0)

| Ex. No. | Polymers | Absorbance (at pH:) 5.2 | 5.6 | 7.0 |
|---|---|---|---|---|
| 61 | 0.1% HD/2% Egalb[a]/1% DxS | 0.437[b] | 0.529[b] | 0.261[b] |
| 62 | 0.1% HD/5% Egalb[c]/1% DxS | 0.293[b] | 0.254[b] | 0.157[b] |
| 63 | 0.1% HD/5% CCP/1% DxS | 1.440 | 1.050 | 0.840 |
| 64 | 0.1% HD/2.5% CCP/1% DxS | 0.453 | 0.347 | 0.140 |
| 65 | 0.1% HD/1% CCP/1% DxS | 0.165 | 0.142 | 0.036 |
| 66 | 0.1% HD/0.5% CCP/1% DxS | 0.054 | 0.042 | 0.035 |
| 67 | 0.1% HD/5% Lys/1% DxS | 1.208 | 0.836 | 0.840 |
| 68 | 0.1% HD/5% P—L—Arg/1% DxS | 0.040 | 0.019 | 0.076 |
| 69C | 0.1% HD/5% PVP/1% DxS | 0.007 | 0.006 | 0.016 |
| 70 | 0.1% HD/5% Mglob/1% DxS | 2.495 | 1.696 | 1.401 |
| 76 | 0.1% HD/5% BSA/0.1% Hep | — | 0.077 | — |
| 77 | 0.1% HD/5% BSA/0.5% Hep | — | 0.055 | — |
| 78 | 0.1% HD/5% BSA/1% Hep | — | 0.087 | — |
| 79C | 0.1% HD/5% BSA/0.1 PVA | — | 0.084 | — |
| 80C | 0.1% HD/5% BSA/0.5% PVA | — | 0.120 | — |
| 81C | 0.1% HD/5% BSA/1% PVA | — | 0.113 | — |
| 82C | 0.1% HD/5% BSA/0.1% DxS$_L$ | — | 0.087 | — |
| 83C | 0.1% HD/5% BSA/0.5% DxS$_L$ | — | 0.052 | — |
| 84C | 0.1% HD/5% BSA/1% DxS$_L$ | — | 0.084 | — |
| 85C | 0.1% HD/5% BSA/1% Dex | 0.503 | 0.360 | 0.474 |
| 86C | 0.1% HD/5% BSA/1% PEG$_L$ | 0.086 | 0.103 | 0.078 |
| 87C | 0.1% HD/5% BSA/1% PEG$_H$ | 0.453 | 0.325 | 0.208 |
| 88C | 0.1% HD/5% BSA/1% PVA | 0.394[b] | 0.408[b] | 0.150 |
| 89 | 0.1% HD/5% BSA/1% DNA | 0.771 | 0.536 | 0.106 |
| 90 | 5% BSA/0.1% HD/1% PVS | 0.529 | 0.399 | 0.099 |
| 91 | 5% BSA/0.1% HD/1% DxS | 0.673 | 0.563 | 0.180 |

[a]crude
[b]precipitate
[c]purified

| Ex. No. | Polymers | 5.2 | 5.6 | 7.0 |
|---|---|---|---|---|
| 92 | 0.1% HD/5% BSA/0.5% PVS | 0.355 | 0.316 | 0.219 |
| 93 | 0.1% HD/5% BSA/1% PVS | 0.529 | 0.399 | 0.099 |
| 94 | 0.1% HD/5% BSA/2% PVS | 0.210[a] | 0.207[a] | 0.225[a] |
| 95C | 0.1% HD/5% BSA/1% CMC$_M$ | 0.113 | | 0.098 |
| 96C | 0.1% HD/5% BSA/0.5% CMC$_M$ | 0.043 | | 0.039 |
| 97C | 0.1% HD/5% BSA/1% CMC$_M$ | 0.052 | | 0.036 |
| 98C | 0.1% HD/5% BSA/0.1% CMC$_M$ | 0.033 | | 0.071 |
| 99C | 0.1% HD/5% BSA/0.01% CMC$_M$ | 0.010 | | 0.022 |
| 100C | 0.1% HD/5% BSA/1% Xan | 0.118 | | 0.207 |
| 101C | 0.1% HD/5% BSA/0.5% Xan | 0.099 | | 0.076 |
| 102C | 0.1% HD/5% BSA/0.25% Xan | 0.075 | | 0.076 |
| 103C | 0.1% HD/5% BSA/0.1% Xan | 0.074 | | 0.032 |
| 104C | 0.1% HD/5% BSA/0.01 Xan | 0.003 | | 0.000 |
| 106 | 0.1% HD/5% BSA/1% DxS | 0.458 | | 0.058 |
| 107C | 0.1% HD/5% BSA[b]/1% DxS | 0.032 | | 0.027 |
| 108C | 0.1% HD/5% BSA/1% DxS/Na$_2$HPO$_4$[c] | 0.024 | | 0.022 |
| 109C | 0.1% HD/5% BSA/1% DxS/TEA[c] | 0.045 | | 0.039 |
| 110C | 0.1% HD/5% BSA/1% DxS/CH(NHOH)$_3$[c] | 0.030 | | 0.044 |
| 111 | 0.1% HD/5% BSA/1% DxS/Na$_2$HPO$_4$[d] | 0.123 | | 0.042 |
| 112 | 0.1% HD/5% BSA/1% DxS/TEA[d] | 0.230 | | 0.037 |
| 113 | 0.1% HD/5% BSA/1% DxS/CH(NHOH)$_3$[d] | 0.230 | | 0.037 |
| 114 | 0.1% HD/5% BSA/1% DxS/NH$_3$[d] | 0.190 | | 0.035 |

[a]precipitate
[b]adjusted to pH 7 with NaOH.
[c]added to initially adjust pH to 7.0
[d]added to initially adjust pH to 6.5

TABLE 3
PHASE DISTRIBUTION DATA

| Ex. No. | Polymers | Material Measured | pH | Phase Measurement[a] Top | Bottom |
|---|---|---|---|---|---|
| 115 | 0.1% HD/5% BSA/1% DxS[b] | All | 6.11 | 0.491[c] | — |
| 116 | 0.1% HD/5% BSA/1% DxS[b] | All | 6.02 | 0.860[c] | — |
| 117 | 0.1% HD/5% BSA/1% DxS[b] | All | 5.5 | — | 0.089[c] |
| 118 | 0.1% HD/5% BSA/1% DxS | BSA[d] | 5.2 | 20.55 | 45.35 |
| 119 | 0.1% HD/5% BSA/1% DxS | BSA[d] | 7.0 | 40.4 | 44.98 |
| 120 | 0.1% HD/5% BSA/1% DxS | BSA[e] | 5.2 | 18.35 | 44.54 |
| 121 | 0.1% HD/5% BSA/1% DxS | BSA[e] | 7.0 | 49.36 | 48.12 |
| 122 | 0.1% HD/5% BSA/1% DxS | DxS[f] | 5.2 | 0.9 | 3.3 |
| 123 | 0.1% HD/5% BSA/1% DxS | DxS[f] | 7.0 | 2.8 | 3.8 |
| 124 | 1 HD%/5% CCP/1% DxS | CCP[d] | 5.2 | 27.25 | 44.54 |
| 125 | 1 HD%/5% CCP/1% DxS | CCP[d] | 7.0 | 33.16 | 48.12 |
| 126 | 0.1% HD/5% CCP/1% DxS | DxS[f] | 5.2 | 2.9 | 3.7 |
| 127 | 0.1% HD/5% CCP/1% DxS | DxS[f] | 7.0 | 3.0 | 3.7 |
| 128C | 5% BSA/1% DxS | BSA[e] | 5.2 | 49.40 | 55.04 |
| 129C | 5% BSA/1% DxS | BSA[e] | 7.0 | 51.05 | 53.76 |
| 130C | 5% BSA/1% DxS | DxS[f] | 5.2 | 3.1 | 3.4 |

TABLE 3-continued

PHASE DISTRIBUTION DATA

| Ex. No. | Polymers | Material Measured | pH | Phase Measurement[a] Top | Bottom |
|---|---|---|---|---|---|
| 131C | 5% BSA/1% DxS | DxS[f] | 7.0 | 3.0 | 3.2 |
| 132 | 0.1% HD/5% BSA/1% DxS | $^{14}$C—HD | 5.6 | 3.8 | 0.2 |
| 133 | 0.1% HD/5% BSA/1% DxS | BSA[e] | 5.6 | 0.176[c] | 0.471[c] |
| 134 | 0.1% HD/5% BSA/1% DxS | $^{14}$C—HD | 5.2 | 1.8 | 0.07 |
| 135 | 0.1% HD/5% BSA/1% DxS | $^{14}$C—HD | 7.0 | 0.76 | 0.11 |
| 136 | 1% HD/5% BSA/1% DxS | $^{14}$C—HD | 5.2 | 0.79 | 0.07 |
| 137 | 1% HD/5% BSA/1% DxS | $^{14}$C—HD | 7.0 | 1.7 | 0.14 |

[a]given in mg/ml and after centrifugation, unless otherwise indicated
[b]in 0.015M HCL
[c]given in absorbance
[d]by Lowry protein method
[e]by rhodamine labelling
[f]by chemical analysis of sulfate Formulations 1–44

Skin Care Compositions

Formulations containing 1% of a 12% aqueous solution of ternary polymer mixtures of HD, BSA and DxS in relative proportion of 0.8:40:1 respectively and having 1.5% GERMABEN, along with skin care additives set forth in Table 5, are made using the following general procedures. The designated formulation is generally provided by forming the designated oil and/or water phases containing the designated additives. When using two phases, the water phase is added to the oil phase with vigorous stirring followed by addition of the designated amount of ternary polymer mixture in aqueous solution with thorough agitation. When appropriate, select additives such as magnesium aluminum silicate are initially provided dispersed as a slurry in water.

The characteristics of the formulations are evaluated for feel, rub-in, after feel of the treated skin, appearance of the skin, along with any other noted characteristics. In some instances, comparisons are made with identical formulations in which the ternary polymer mixture is omitted or replaced with an equal concentration of BSA only. For example, analysis of the non-ionic lotion of Formulation No. 15 containing ternary polymer mixture provides a smoother feel to the skin as well as decreased resistance during rub-in as compared to skin treated with the same formulation without ternary polymer mixture or replaced with BSA. Similarly, the clear eye gel of Formulation No. 29, provides a better after feel as well as providing a film with a less rigid appearance as compared with the same gel but which contains BSA in place of the ternary polymer mixture. Also, nonionic foundation makeup of Formulation No. 44 provides a light, smooth, matte finish whereas control with BSA exhibits a tacky rub-in and whereas the same formulation without the ternary polymer mixture gives a shiny finish with uneven coverage on the skin. Night cream Formulations Nos. 27 and 28 exhibit less oiliness as compared to such formulations without ternary polymer mixture. Facial toner Formulations Nos. 37–42 exhibit reduced "sting" associated with alcohol content, as well as improved skin feel and smoother skin surface appearance as compared, to such formulations without the ternary polymer mixture or instead using BSA only.

TABLE 4

FORMULATIONS

| Type: | THIN LOTIONS | | | | | | | | | CLEANSING |
|---|---|---|---|---|---|---|---|---|---|---|
| Formulation No. | 1 | 2 | 3 | 4 | 5 | 6 | 7 | 8 | 9 | 10 |
| Oil Phase: | | | | | | | | | | |
| ACETULAN ® | | | | | | 1 | | | | |
| AMERCHOL ® L101 | | | | | | 3 | | | | |
| AMERLATE ® P | | | | | | | 0.5 | 0.5 | 0.5 | |
| Beeswax | | | | | | | 0.5 | 0.5 | 0.5 | 2 |
| Cetyl Alcohol | | | 4 | 4 | 4 | | | | | |
| GLUCATE ® SS | 1 | 1 | 1 | 1 | 1 | 0.5 | 1.5 | 1.5 | 1.5 | 1.2 |
| Mineral Oil | 6 | 6 | 6 | 6 | 6 | | | | | 16 |
| MODULAN | 2 | 2 | 2 | 4 | 4 | | | | | |
| PROMULGEN ® D | | 2.5 | | | 2 | | 4 | 4 | 4 | |
| PROMULGEN ® G | | | | | | 4 | | | | |
| Solulan C-24 | | | | | | 0.25 | | | | |
| Spermwax | | | | | | | | | | 2 |
| Stearyl Alcohol | 2 | 2 | | | | | | | | |
| Water Phase: | | | | | | | | | | |
| BSA/DxS/HD | 1 | 1 | 1 | 1 | 1 | 1 | 1 | 0.5 | 2 | 1 |
| GERMABEN ® II | | | | | | | 1 | 1 | 1 | |
| CARBOPOL ® 941* | | | | | | | | | | 7 |
| GERMABEN ® IIE | 1 | 1 | 1 | 1 | 1 | 1 | | | | 1 |
| GLUCAM ® E-10 | | | | | | 5 | 15 | 15 | 15 | |
| GLUCAM ® E-20 | 3 | 3 | 3 | 3 | 3 | | | 0.5 | 0.5 | |
| GLUCAMATE ® SSE-20 | 1.5 | 1.5 | 1.5 | 1.5 | 1.5 | 1.5 | 0.5 | | | 2 |
| TEA (10% aqueous) | | | | | | | | | | 2 |
| Water | 82.5 | 80.0 | 80.5 | 78.5 | 76.5 | 82.75 | 76.5 | 77 | 75.5 | 65.8 |
| pH: | 5.6 | 5.7 | 6.7 | | | 6.0 | 6.0 | 6.0 | 6.0 | 6.9 |
| Type: | MEDIUM LOTIONS | | | | MED-HI VISCOSITY CREAM | | | | | |
| Formulation No. | 11 | 12 | 13 | 14 | 15 | 16 | 17 | 18 | 19 | |

TABLE 4-continued

FORMULATIONS

| Oil Phase: | | | | | | | | | |
|---|---|---|---|---|---|---|---|---|---|
| ACETULAN ® | | 2 | 2 | 2 | | | | | |
| AMEROXOL ® OE-2 | | | | | 1 | 1 | 1 | 1 | 1 |
| Cetyl Alcohol | 0.5 | 2 | 2 | 2 | 2 | 2 | 2 | 2 | 2 |
| Dimethicone 200, 350 | | | | | 1 | 1 | 1 | 1 | 1 |
| GLUCAM ® E-20 DS | | | | | 1 | 1 | 1 | 1 | 1 |
| GLUCATE ® SS | 0.5 | 1 | 2 | 1 | 2 | 2 | 2 | 2 | 2 |
| Glycerol Monostearate, Neut. | | 0.5 | 0.5 | 1.5 | | | | | |
| Mineral Oil | 5 | | | | 4 | 4 | 4 | 4 | 4 |
| PROMULGEN ® D | | | | | 5 | | 3 | 5 | 5 |
| Sesame Oil | | 10 | 10 | 10 | | | | | |
| Water Phase: | | | | | | | | | |
| BSA/DsX/HD | 1 | 1 | 1 | 1 | 1 | 1 | 1 | 4 | 2 |
| CARBOPOL ® 934* | 10 | | | | | | | | |
| GERMABEN ® IIE | 1 | 1 | 1 | 1 | 1 | 1 | 1 | 1 | 1 |
| GLUCAM ® E-20 | 3 | 3 | 3 | 3 | | | | | |
| GLUCAMATE ® SSE-20 | 1.5 | 3 | 3 | 3 | 2 | 2 | 2 | 2 | 2 |
| Water | 77.5 | 76.5 | 75.5 | 75.5 | 80 | 85 | 82 | 77 | 79 |
| pH: | 7.3 | 5.8 | 6.9 | 7.0 | 6.2 | 6.2 | 6.8 | 6.0 | 6.0 |

| Type: | MEDIUM CREAMS | | | | | | | NIGHT CREAMS | |
|---|---|---|---|---|---|---|---|---|---|
| Formulation No. | 20 | 21 | 22 | 23 | 24 | 25 | 26 | 27 | 28 |
| Oil Phase: | | | | | | | | | |
| ACETULAN ® | 1.5 | 1.5 | 1.5 | 1.5 | 1.5 | | | 3 | 3 |
| AMERCHOL ® L-101 | 1.5 | 1.5 | 1.5 | 1.5 | 1.5 | | | 3 | 3 |
| Beeswax | | | | | | | | 3 | 5 |
| Cetyl Alcohol | | | | 3 | | | | | |
| GLUCATE ® SS | | | 0.5 | | 1.5 | 2 | 2 | | |
| Mineral Oil | 1.5 | 1.5 | 1.5 | 1.5 | 1.5 | 2 | 2 | 5 | 5 |
| Modulan | 3 | 3 | 3 | 3 | 4 | | | | |
| Petrolatum | | | | | | | | 3 | 3 |
| PROMULGEN ® D | 5 | 5 | 5 | 5 | 5 | | | 8 | 8 |
| PROMULGEN ® G | | | | | | 5 | 5 | | |
| SOLULAN ® 5 | | | | | | 0.5 | 0.5 | | |
| Stearyl Alcohol | | 2 | | | | | | 2 | |
| Water Phase: | | | | | | | | | |
| BSA/DxS/HD | 1 | 1 | 1 | 1 | 1 | 0.5 | 1 | 1 | 1 |
| GERMABEN ® II | | | | | | 1 | 1 | | |
| GERMABEN ® IIE | 1 | 1 | 1 | 1 | 1 | | | 1 | 1 |
| GLUCAM ® E-10 | | | | | | 3.5 | 3.5 | 3 | 3 |
| GLUCAMATE ® SSE-20 | | | | | | 2 | 2 | | |
| Water | 85.5 | 83.5 | 85 | 82.5 | 83 | 83.5 | 83 | 68 | 68 |
| pH: | 5.8 | 5.8 | 6.8 | 6.8 | 6.0 | 6.0 | 6.0 | 5.4 | 5.9 |

| Type: | Facial Gels | | Clear Eye Gels | | After Sun Aloe Gel | After Sun Aloe Creams | | |
|---|---|---|---|---|---|---|---|---|
| Formulation No. | 29 | 30 | 31 | 32 | 33 | 34 | 35 | 36 |
| Water Phase: | | | | | | | | |
| Aloe Extract | | | | | | 15 | 15 | 5 |
| Aloe Gel | | | | | 2 | | | |
| BSA/DxS/HD | 1 | 1 | 1 | 1 | 1 | 1 | 1 | 1 |
| CARBOPOL ® 934* | | | | | | 25 | | |
| CARBOPOL ® 940* | | | 25 | 25 | 25 | | 25 | 25 |
| GERMABEN ® IIE | 1 | | 0.5 | 0.5 | 0.5 | 1 | 1 | 1 |
| GERMALL ® II | | 0.15 | | | | | | |
| GLUCAM ® E-10 | 2 | 2 | | 5 | 5 | 5 | 5 | 5 |
| Glycerin | 2 | 2 | | | | | | |
| Methyl Paraben | | 0.05 | | | | | | |
| CELLOSIZE ® PCG-10 | 1 | 0.5 | | | | | | |
| SOLULAN ® 75 | | | | | | 2 | 2 | 2 |
| TEA (10% aqueous) | | | 11.25 | 11.25 | 11.25 | 11.2 | 11.2 | 11.25 |
| Water | 93 | 94.3 | 62.25 | 57.25 | 55.25 | 39.8 | 39.8 | 49.75 |
| pH: | 5.9 | 5.6 | 6.9 | 6.5 | 6.0 | 6.9 | 6.9 | 6.0 |

*3% aqueous

| Type: | Facial Toners | | | | | | Hydroalcoholic Aftershave | Foundation Make-up |
|---|---|---|---|---|---|---|---|---|
| Formulation No. | 37 | 38 | 39 | 40 | 41 | 42 | 43 | 44 |
| Oil Phase: | | | | | | | | |
| AMEROXOL ® OE-2 | | | | | | | | 2 |
| Cetyl Alcohol | | | | | | | | 1.5 |
| Cetyl Palmitate | | | | | | | | 2.5 |
| Dimethicone 200, 300 | | | | | | | | 2 |
| Glyceryl Stearate, SE | | | | | | | | 5 |
| Isopropyl Isostearate | | | | | | | | 10 |
| OHLAN ® | | | | | | | | 1 |
| SOLULAN ® PB-10 | | | | | | | | 3 |

TABLE 4-continued

FORMULATIONS

|  | 1 | 2 | 3 | 4 | 5 | 6 | 7 | 8 |
|---|---|---|---|---|---|---|---|---|
| SOLULAN ® 98 |  |  |  |  |  |  |  | 4 |
| Stearyl Alcohol |  |  |  |  |  |  |  | 1.5 |
| Water Phase: |  |  |  |  |  |  |  |  |
| BSA/DxS/HD | 1 | 1 | 1.5 | 1.7 | 2 | 5 | 1.0 | 1 |
| GERMABEN ® IIE |  |  |  |  |  |  |  | 1 |
| GLUCAM ® P-20 | 3 |  |  |  |  |  |  |  |
| Menthol | 0.3 | 0.3 | 0.3 | 0.3 | 0.3 | 0.3 | 0.1 |  |
| Mg Al Silicate* |  |  |  |  |  |  |  | 25 |
| Pigment |  |  |  |  |  |  |  | 10 |
| Propylene Glycol |  |  |  |  |  |  |  | 5 |
| TEA (10% Aq.) |  |  |  |  |  |  | 0.2 |  |
| Water | 53.7 | 48.35 | 48.1 | 48.0 | 47.85 | 46.35 | 38.7 | 25.5 |
| Witch Hazel | 2 | 2 | 2 | 2 | 2 | 2 |  |  |
| SDA 40 Alcohol | 40 | 48.35 | 48.1 | 48.0 | 47.85 | 46.35 | 60 |  |
| pH: | 6.2 | 6.0 | 6.0 | 6.0 | 6.0 | 6.0 | 6.0 | 7.2 |

*4% aqueous

Photographic Analysis

Ternary polymer mixtures containing 0.1% HD, 5% BSA and 1% DxS in aqueous solution applied to skin and other substrates are presented in the drawings. The pH of the initial solution is adjusted using a 1M phosphate buffer to 7.0, as shown on the right of FIGS. 1 to 3, and using 1M acetate buffer to 5.2, as shown on the left of FIGS. 1 to 3.

FIG. 1 is a photograph of the ternary polymer mixture along with 1% glycerol applied to SARAN ® Wrap, i.e., polyvinylidene chloride providing a dry film. As is clearly apparent from the photograph, the ternary polymer mixture provides an opaque film under the acidic pH 5.2 conditions while remaining clear under the neutral pH 7.0 conditions.

Figure 2:
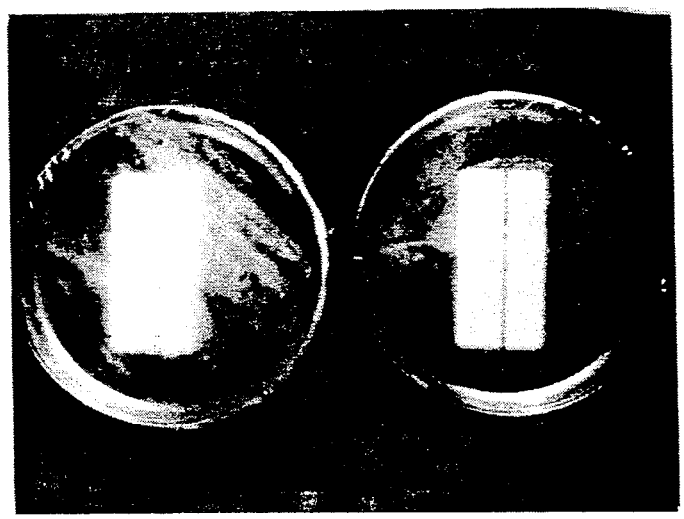
Figure 3:
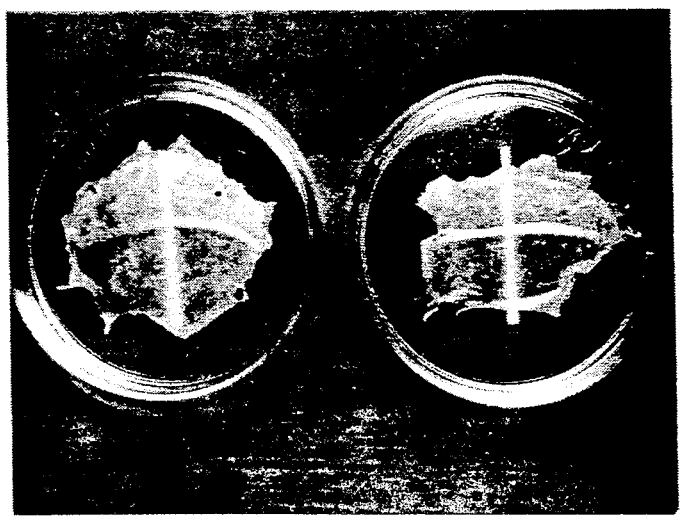

FIGS. 2 and 3 demonstrate the masking effect of the ternary polymer mixture under acidic versus neutral conditions. In FIG. 2, a film of the ternary polymer mixture is formed on Polyvinylidene chloride which is placed over a white slip marked with a black line. As clearly shown in FIG. 2, the film under acidic, i.e. pH 5.2, conditions masks the background as compared to the substantially clear film under neutral i.e. pH 7.0, conditions. The results shown in FIG. 3, using stratum corneum membrane in place of the polyvinylidene chloride and a narrow, white strip in the background, also demonstrates the masking effect of the ternary polymer mixture applied to skin under acidic versus neutral conditions.

Figure 4:
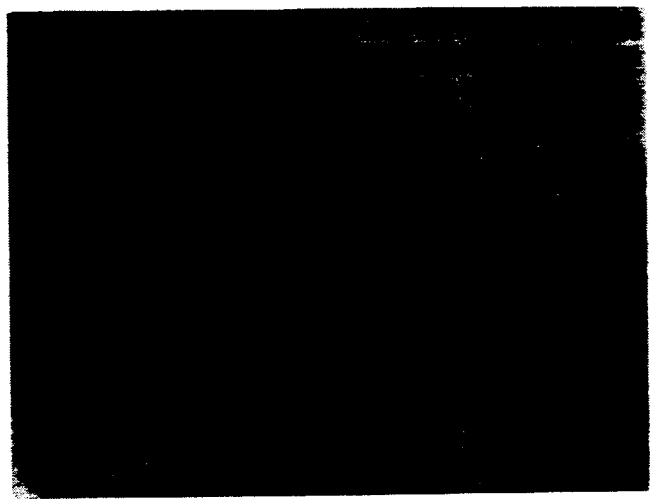
Figure 5:
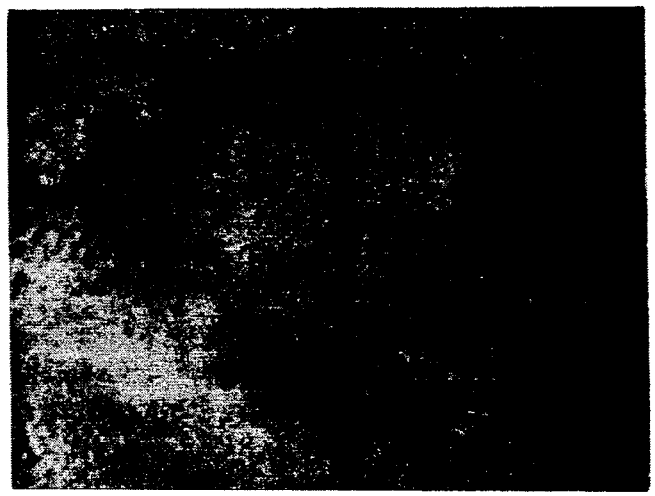
Figure 6:
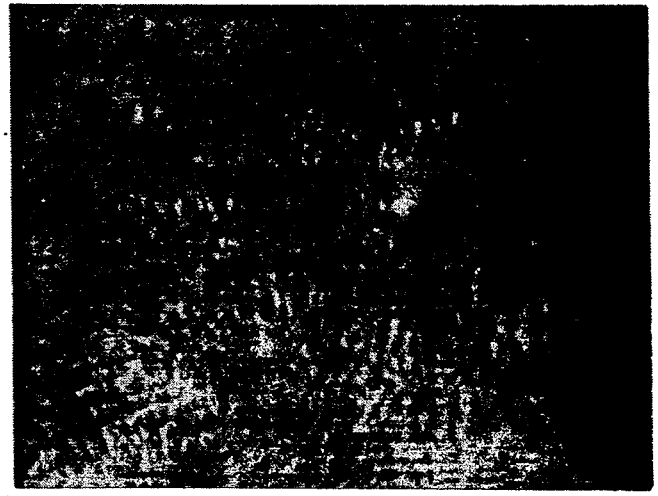

FIGS. 4 through 8 are photographs of human skin before and after application of various polymer compositions. FIG. 4 is a photograph of an area of skin prior to application of a 10% aqueous solution of BSA. After four applications of BSA, progressive whitening, cracking and overall non-aesthetic film appearance arise as shown in FIG. 5. FIG. 6 is a photograph of the treated skin shown in FIG. 5 but after the skin is stretched and shows undesirable stretch marks and cracking, characteristic of BSA films. FIG. 7 is a photograph of skin prior to application of a 12% aqueous solution of ternary polymer mixture of HD, BSA and DxS in a relative proportion of 0.1:5:1 respectively. FIG. 8 is a photograph of the same area of skin in FIG. 7 treated with four applications of the ternary polymer mixture, and then stretched, which did not change the appearance of the film, which mixture provides a smooth, non-shiny and acceptable feel as well as masking.

We claim:

1. An aqueous composition consisting essentially of water and a tertiary polymer mixture of components selected from each of the following groups:
   (1) albumin;
   (2) a polynucleotide or a polycarboxylate having a molecular weight of at least about 100,000; and
   (3) a polysulfate or a polysulfonate containing acidic groups with a $pK_a$ of less than about 3 in an amount sufficient to provide an equivalent weight of such acidic groups of less than about 1,000;

said components being present in amounts sufficient to cause a decrease in light transmission through an aqueous solution of the mixture under acidic as compared to neutral conditions.

2. The compositions of claim 1 wherein:
   (1) the albumin is serum albumin;
   (2) the polycarboxylate is hyaluronan or derivatives thereof which contain a repeating disaccharide structure of D-glucuronic acid and 2-acetamido-2-desoxy-D-glucose joined by alternating $\beta$1-3 glucoronidic and $\beta$1-4 glucosaminidic bonds; and
   (3) the polysulfate is dextran sulfate.

3. The composition of claim 1 wherein said components are present in amounts effective to cause an increase in the turbidity of the composition under acidic as compared to neutral conditions.

4. The composition of claim 1 wherein said components are present in amounts effective to cause an additional phase to form when the pH of the composition is changed from neutral to acidic conditions.

5. The composition of claim 1 wherein said components are present in amounts effective to cause an increase in the light absorbance of the composition of at least 0.1 at 540 nanometers when the pH of the composition is reduced from 7.0 to 5.2.

6. A skin care composition consisting essentially of a carrier and a ternary polymer mixture of components selected from each of the following groups:
   (1) albumin;
   (2) a polycarboxylate having a molecular weight of at least about 100,000; and
   (3) a polysulfate, a polysulfonate or a polynucleotide containing acidic groups with a $pK_a$ of less than about 3 in an amount sufficient to provide an equivalent weight of such acidic groups of less than about 1,000;

said components being present in amounts sufficient to cause a decrease in light transmission through an aqueous solution of the mixture under acidic as compared to neutral conditions.

7. The composition of claim 6 wherein the carrier is selected from water, water-in-oil emulsions, oil-in-water emulsions, alcohols, glycols or combinations thereof.

8. The composition of claim 6 which further comprises a skin care additive.

9. The composition of claim 6 wherein the polysulfate, polysulfonate or polynucleotide of group (3) has an anionic charge density of from about 100 to 500.

10. The composition of claim 6 wherein the weight ratio of the albumin of group (1) to the polycarboxylate of group (2) is from about 0.05:1 to 100:1.

11. The composition of claim 6 wherein the weight ratio of the albumin of group (1) to the polysulfate, polysulfonate or polynucleotide of group (3) is from about 1:1 to 200:1.

12. The composition of claim 6 wherein the weight ratio of the polysulfate, polysulfonate or polynucleotide of group (3) to the polycarboxylate of group (2) is from about 0.1:1 to 100:1.

13. A process for diminishing the appearance of wrinkles of the skin which comprises applying to the skin a composition consisting essentially of a carrier and a ternary polymer mixture of components selected from each of the following groups:
   (1) albumin;
   (2) a polycarboxylate having a molecular weight of at least about 100,000; and
   (3) a polysulfate, a polysulfonate or a polynucleotide containing acidic groups with a $pK_a$ of less than about 3 in an amount sufficient to provide an equivalent weight of such acidic groups of less than about 1,000;

said components being present in amounts sufficient to cause an increase in the turbidity of the composition when applied to the skin.

14. The process of claim 13 wherein:
   (1) the albumin is serum albumin;
   (2) the polycarboxylate is hyaluronan or derivatives thereof which contain a repeating disaccharide structure of D-glucuronic acid and 2-acetamido-2-desoxy-D-glucose joined by alternating $\beta$1–3 glucoronidic and $\beta$1–4 glucosaminidic bonds; and
   (3) the polysulfate is dextran sulfate.

* * * * *